(12) United States Patent
Kroll et al.

(10) Patent No.: US 8,398,994 B2
(45) Date of Patent: Mar. 19, 2013

(54) LAWSONIA VACCINE AND METHODS OF USE THEREOF

(75) Inventors: Jeremy Kroll, Urbandale, IA (US); Michael Roof, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days.

(21) Appl. No.: 11/457,039

(22) Filed: Jul. 12, 2006

(65) Prior Publication Data

US 2007/0014815 A1 Jan. 18, 2007

Related U.S. Application Data

(60) Provisional application No. 60/699,946, filed on Jul. 15, 2005.

(51) Int. Cl.
*A61K 39/02* (2006.01)
(52) U.S. Cl. ............ 424/234.1; 424/93.4; 424/825; 435/252.1
(58) Field of Classification Search .................. None
See application file for complete search history.

(56) References Cited

U.S. PATENT DOCUMENTS

| | | | |
|---|---|---|---|
| 3,479,430 A * | 11/1969 | Welter | 424/223.1 |
| 3,907,987 A * | 9/1975 | Wilson | 424/257.1 |
| 4,132,597 A | 1/1979 | Kvanta | |
| 4,237,218 A | 12/1980 | Monthony et al. | |
| 4,880,739 A | 11/1989 | Yamada et al. | |
| 4,904,597 A | 2/1990 | Inoue et al. | |
| 4,920,048 A | 4/1990 | Diderichsen | |
| 5,126,265 A | 6/1992 | Cidaria et al. | |
| 5,192,679 A | 3/1993 | Dawson et al. | |
| 5,230,912 A | 7/1993 | Yajima et al. | |
| 5,296,221 A | 3/1994 | Mitsuoka et al. | |
| 5,318,908 A | 6/1994 | Seki et al. | |
| 5,338,670 A | 8/1994 | Sekura et al. | |
| 5,380,657 A | 1/1995 | Schaefer et al. | |
| 5,436,001 A | 7/1995 | Kramer | |
| 5,610,059 A | 3/1997 | Joens et al. | |
| 5,714,375 A | 2/1998 | Knittel et al. | |
| 5,885,823 A * | 3/1999 | Knittel et al. | 435/243 |
| 6,414,036 B1 | 7/2002 | Ninkov | |
| 6,605,696 B1 | 8/2003 | Rosey | |
| 6,649,660 B2 | 11/2003 | Ninkov | |
| 6,921,536 B2 | 7/2005 | Jacobs et al. | |
| 6,982,314 B2 | 1/2006 | Rosey | |
| 7,022,328 B1 | 4/2006 | Panaccio et al. | |
| 7,052,697 B1 | 5/2006 | Hasse et al. | |
| 7,312,065 B2 | 12/2007 | Roof et al. | |
| 7,550,270 B2 | 6/2009 | Kroll et al. | |
| 7,758,870 B2 | 7/2010 | Roof et al. | |
| 2002/0103261 A1 | 8/2002 | Ninkov | |
| 2003/0021802 A1* | 1/2003 | Rosey | 424/190.1 |
| 2003/0087421 A1 | 5/2003 | Gebhart et al. | |
| 2003/0157120 A1 | 8/2003 | Panaccio et al. | |
| 2005/0031647 A1 | 2/2005 | Roof et al. | |
| 2005/0069559 A1 | 3/2005 | Jacobs et al. | |
| 2005/0143561 A1 | 6/2005 | Rosey | |
| 2006/0024696 A1 | 2/2006 | Kapur et al. | |
| 2006/0171690 A1 | 8/2006 | Chu et al. | |
| 2006/0204522 A1 | 9/2006 | Kroll et al. | |
| 2006/0286118 A1 | 12/2006 | Vermeij | |
| 2007/0014815 A1 | 1/2007 | Kroll et al. | |
| 2007/0212373 A1 | 9/2007 | Vermeij | |
| 2008/0063648 A1 | 3/2008 | Kroll | |
| 2008/0112980 A1 | 5/2008 | Roof et al. | |
| 2008/0226669 A1 | 9/2008 | Roof et al. | |
| 2008/0241190 A1 | 10/2008 | Kroll et al. | |
| 2008/0279893 A1 | 11/2008 | Vaughn et al. | |
| 2009/0215698 A1 | 8/2009 | Schaeffer et al. | |
| 2010/0062021 A1 | 3/2010 | Winkelman | |
| 2010/0266637 A1 | 10/2010 | Deitmer et al. | |

FOREIGN PATENT DOCUMENTS

| | | |
|---|---|---|
| EP | 1219711 A2 | 7/2002 |
| EP | 1403643 A1 | 3/2004 |
| EP | 1586646 A2 | 10/2005 |
| WO | 9407531 | 4/1994 |
| WO | 9639629 | 12/1996 |
| WO | 9720050 A1 | 6/1997 |
| WO | 0189559 | 11/2001 |
| WO | 0226250 A2 | 4/2002 |
| WO | 03006665 A1 | 1/2003 |
| WO | 2004033631 A2 | 4/2004 |
| WO | 2005011731 | 2/2005 |
| WO | 2005070958 A2 | 8/2005 |
| WO | 2006020730 A2 | 2/2006 |
| WO | 2006099561 A1 | 9/2006 |
| WO | 2006113782 A2 | 10/2006 |
| WO | 2006116763 A2 | 11/2006 |
| WO | 2007011993 A1 | 1/2007 |
| WO | 2007140244 A2 | 12/2007 |
| WO | 2008063959 A1 | 5/2008 |
| WO | 2009037262 A2 | 3/2009 |

OTHER PUBLICATIONS

Wittman et al. Archives of Virology 60, 33-42 1979.*
Pensaert et al. Veterinary Microbiology 1998 (2004) 175-183.*
Nelson et al. (The Journal of Experimental Medicine vol. 56, p. 835-840, 1932).*
Nelson et al (The Journal of Experimental Medicine vol. 60, p. 287-291, 1934.*
Vaccines How They Work, Why They Fail http://www.nationalhogfarmer.com/mag/farming_vaccines_work_why/index.html (Apr. 15, 2003. Retrieved online Jun. 16, 2008).*
Desrosiers et al (Experiences with the use of Enterisol Ileitis in Canadian Breeding Animals. Ileitis Symposium, Hamburg, Jun. 28, 2004 obtained on Jan.6, 2009 from http://www.animal-health-online.de/drms/Vortrag_Desrosiers.pdf ) pp. 1-4.*

(Continued)

*Primary Examiner* — Oluwatosin Ogunbiyi
(74) *Attorney, Agent, or Firm* — Michael P. Morris; Joyce L. Morrison

(57) ABSTRACT

The present invention provides improved vaccination methods for increased protection against ileitis. The methods provide for the vaccination of young animals, preferably piglets, between 10 and 26 days of age, vaccination of pregnant sows during the second or third stages of gestation, and a combination of these methods. Vaccination of the pregnant sows can occur using repeated and/or high doses of *Lawsonia* antigen prior to farrowing.

19 Claims, No Drawings

OTHER PUBLICATIONS

Vaccination Guidelines for Swine Jun. 2004 obtained on Jan. 6, 2009 from http://www.vido.org/pdf/vstg_pubs/Vaccination%20Guidelines_SWINE_.june18.2004-tl1.pdf), pp. 1-25.*

Walter et al J Swine Health Prod. 2004;12(6):310-313.*

Vaccination Guidelines for Swine Jun. 2004 obtained on Jan. 6, 2009 from http://www.vido.org/pdf/vstg_pubs/Vaccination%20Guidelines_SWINE_.june18.2004-tl1.pdf), pp. 1-25.*

Product information for Enterisol® SC-54 dated May 2003.*

Product insert for Enterisol Ileitis ®0 vaccine dated Jan. 2005.*

Kroll et al. Proceedings of the 18th IPVS Congress, Hamburg, Germany, Jun. 27-Jul. 1, 2004 (Proc IPVS. Hamburg, Germany. 2004:255).*

Pozo et al. Proceedings of the 17th IPVS Congress, Ames, Iowa, 2002, 2:205.*

McOrist et al., "In Vitro and In-Life Studies of Efficacy of Valnemulin for Proliferative Enteropathy (ILEITIS)". Proceedings of the 15th IPVS Congress, Birmingham, England, Jul. 1998, p. 114.

McOrist et al., "In vitro testing of antimicrobial agents for proliferative enteropathy (ileitis)". Swine Health and Production, vol. 3, No. 4, Jul. and Aug. 1995, pp. 146-149.

McOrist et al., "Monoclonal antibodies to intracellular campylobacter-like organisms of the porcine proliferative enteropathies". The Veterinary Record, vol. 121, No. 18, Oct. 1987, pp. 421-422.

McOrist et al., "Oral administration of tylosin phosphate for treatment and prevention of proliferative enteropathy in pigs". Advanced Journal of Veterinary Research, vol. 58, No. 2, Feb. 1997, pp. 136-139.

McOrist et al., "Polymerase chain reaction for diagnosis of porcine proliferative enteropathy". Veterinary Microbiology, vol. 41, No. 3, 1994, pp. 205-212.

McOrist et al., "Porcine Proliferative Enteropathy". The Veterinary Record, vol. 132, No. 14, Apr. 1993, p. 368.

McOrist et al., "Reproduction of Porcine Proliferative Enteropathy with Pure Cultures of Ileal Symbiont Intracellularis". Infection and Immunity, vol. 61, No. 10, Oct. 1993, pp. 4286-4292.

McOrist et al., "Synergism of ileal symbiont intracellularis and gut bacteria in the reproduction of porcine proliferative enteropathy". The Veterinary Record, vol. 134, No. 13, Mar. 1994, pp. 331-332.

McOrist et al., "The Treatment of Induced Porcine Proliferative Enteropathy (ILEITIS) with Tylosin Tartrate (TYLAN® Soluble, Elanco) Administered Via Drinking Water". Proceedings of the 15th IPVS Congress, Birmingham, England, Jul. 1998, p. 118.

McOrist et al., "Treatment and prevention of porcine proliferative enteropathy with oral tiamulin". The Veterinary Record, vol. 139, Dec. 1996, pp. 615-618.

Nielsen et al., ":The serological response to *Salmonella serovars* typhimurium and infantis in experimentally infected pigs. The time course followed with an indirect anti-LPS ELISA and bacteriological examinations". Veterinary Microbiology, vol. 47, 1995, pp. 205-218.

Oka et al., "Large-Scale Animal Cell Culture: A Biological Perspective". Large-Scale Mammalian Cell Culture, Marcel Dekker, Inc., New York and Basel, 1990, pp. 71-73.

Peace et al., "Comparative Analysis of the 16S rRNA Gene Sequence of the Putative Agent of Proliferative Ileitis of Hamsters". International Journal of Systematic Bacteriology, vol. 44, No. 4, Oct. 1994, pp. 832-835.

Reuveny, S., "Microcarrier Culture Systems". Bioprocess Technology, vol. 10, 1990, pp. 271-341.

Reuveny, S., "Microcarriers in Cell Culture Structure and Applications". Advances in Cell Culture, vol. 4, 1985, pp. 213-247.

Rowland et al., "Intestinal Adenomatosis in the Pig: Occurrence of a Bacterium in Affected Cells". Nature, vol. 243, Jun. 1973, p. 417.

Rowland et al., Porcine intestinal adenomatosis: A possible relationship with necrotic enteritis, regional ileitis and proliferative haemorrhagic enteropathy. Veterinary Records, vol. 97, 1975, pp. 178-180.

Schoeb et al., "Enterocecocolitis Associated with Intraepithelial Campylobacter-like Bacteria in Rabbits (*Oryctolagus cuniculus*)". Veterinary Pathology, vol. 27, 1990, pp. 73-80.

Schultheiss, P.C., "A Study of the Pathogenicity of Campylobacter Species in Swine". A Thesis Submitted to the Faculty of the Graduate School of the University of Minnesota, Jun. 1987, pp. 1-287.

Senk et al. "Proliferative typhlocolitis—the fifth form of the procine intestinal adenomatosis complex". Proceedings, International Pig Veterinary Society, 11th Congress, Jul. 1-8, 1990, Lausanne, Switzerlandk, 1990, p. 113.

Spier et al., "Trypsinization of BHK 21 Monolayer Cells Grown in Two Large-Scale Unit Process Systems". Biotechnology and Bioengineering, vol. XIX, 1977, pp. 1735-1738.

Stills, H.F., "Isolation of an Intracellular Bacterium from Hamsters (*Mesocricetus auratus*) with Proliferative Ileitis and Reproduction of the Disease with a Pure Culture". Infection and Immunity, vol. 59, No. 9, Sep. 1991, pp. 3227-3236.

Tam et al., "Eukaryotic Cells Grown on Microcarrier Beads Offer a Cost-Efficient Way to Propagate *Chlamydia trachomatis*". BioTechniques, vol. 13, No. 3, 1992, pp. 374-378.

Tseneva et al., "Invasiveness and cytotoxicity as criteria in assessing *Yersinia* attenuation". Zhurnal Mikrobiologii, Epidemiologii, i Immunobiologii, vol. 10, No. 6, Sep. 1988, pp. 10-16, Abstract Only.

Walter et al., "Serologic profiling and vaccination timing for *Lawsonia intracellularis*". Journal of Swine Health and Production, vol. 12, No. 6, 2004, pp. 310-313.

Ward et al., "Diagnosing, treating, and controlling proliferative enteritis in swine". Veterinary Medicine, Food-Animal Practice, Mar. 1990, pp. 312-318.

Ward et al., "Reproduction of proliferative enteritis in pigs fed embryonated eggs inoculated with proliferative enteritis tissues". Proceedings, International Pig Veterinary Society, 11th Congress, Jul. 1-5, 1990, Lausanne, Switzerland, p. 116.

Wiuff et al., "Immunochemical analyses of serum antibodies from pig herds in a *Salmonella* non-endemic region". Veterinary Microbiology, vol. 85, 2002, pp. 69-82.

Yates et al., "Proliferative Hemorrhagic Enteropathy in Swine: An Outbreak and Review of Literature". Canadian Veterinary Journal, vol. 20, Oct. 1979, pp. 261-268.

Starek, et al., Sows seropositive to *Lawsonia intracellularis*(LI) influence performance and LI seropositivity of their offspring. ACTA Vet. BRNO, vol. 73, No. 3, Sep. 2004, pp. 341-345.

Barna, et al., Effect of gilt seropositivity to *Lawsonia intracellularis*(LI) on their offspring's seropositivity to LI and on diarrhea after a pure-culture challenge. Preventive Veterinary Medicine, vol. 61, No. 1, Sep. 30, 2003, pp. 71-78.

Kroll, et al., Evaluation of protective immunity in pigs following oral administration of an avirulent live vaccine of *Lawsonia intracellularis*. American Journal of Veterinary Research, vol. 65, No. 5, May 5, 2004, pp. 559-565.

Walter, et al., Serologic profiling and vaccination timing for *Lawsonia intracellularis*. Journal of Swine Health and Production, American Association of Swine Veterinarians, US, vol. 12, 2004, pp. 310-313.

International Search Report and Written Opinion for PCT/US2006/027981 mailed Dec. 13, 2006.

"Multicomponent Vaccine Development". NIH Guide, vol. 22, No. 28, Aug. 1993, Retrieved from URL: http://grants.nih.gov/grants/guide/rfa-files/RFA-AI-93-017.html, Retrieved on Nov. 20, 2006, 9 pages.

Alderton et al., "Experimental Reproduction of Porcine Proliferative Enteritis". Journal of Comparative Pathology, vol. 106, 1992, pp. 159-167.

Armbruster et al., "Evaluation of Enterisol® Li Ileitis Vaccine and Tylan® Premix Efficacy Against Porcine Proliferative Enteropathy in a Challenge Model". Proceedings of the 18th International Pig Veterinary Society Congress, vol. 2, Hamburg, Germany, 2004, p. 579.

Birch et al., "Suspension Culture of Mammalian Cells". Large-Scale Mammalian Cell Culture, Marcel Dekker, Inc., New York and Basel, 1990, pp. 258-270.

Boesen et al., "Development, characterization and diagnostic application of a monoclonal antibody specific for a proteinase K resistant Lawsonia intracellularis antigen". Veterinary Microbiology, vol. 105, 2006, pp. 199-206.

Boesen et al., "Evaluation of a novel enzyme-linked immunosorbent assay for serological diagnosis of porcine proliferative enteropathy". Veterinary Microbiology, vol. 109, 2005, pp. 105-112.

Boosinger et al., "Campylobacter sputorum subsp mucosalis and Campylobacter hyointestinalis infections in the intestine of gnotobiotic pigs". American Journal of Veterinary Research, vol. 46, No. 10, Oct. 1985, pp. 2152-2156.

Bornhorn, R., "Efficacy and economical impact of oral vaccination of partially infected piglets with Enterisol® Ileitis". Praktischer Tierarzt, vol. 88, No. 3, 2007, p. 172.

Brock et. al., "Immunization for Infectious Disease". Biology of Microorganisms, Ch. 16, PrenticeHall, Inc., 4th Ed., (19), 1984, pp. 557-558.

Chang et al., "Campylobacter hyointestinalis, a possible cause of proliferative enteritis in swine". Campylobacter II. Proceedings of the Second International Workshop on Campylobacter Infections, Brussels, Sep. 6-9, 1983, p. 131.

Chang et al., "Immunofluorescent demonstration of Campylobacter hyointestinalis and Campylobacter sputorum subsp mucosalis in swine intestines with lesions of proliferative enteritis". American Journal of Veterinary Research, vol. 45, No. 4, Apr. 1984, pp. 703-710.

Fattom et al., "Epitopic overload at the site of injection may result in suppression of the immune response to combined capsular polysaccharide conjugate vaccines". Vaccine, vol. 17, 1999, pp. 126-133.

Finn, D.L., "Isolation and characterization of viral agents associated with porcine proliferative enteritis". A Thesis Submitted to the faculty of the Department of Microbiology and Immunology in Partial Fulfillment of the Requirements for the Degree of Master of Science with a Major in Microbiology, The University of Arizona, 1987, pp. 1-86.

Finter et al., "Large-Scale Mammalian Cell Culture: A Perspective". Large-Scale Mammalian Cell Culture, Marcel Dekker, Inc., New York and Basel, 1990, pp. 1-14.

Fox et al., "Campylobacter-like Omega Intracellular Antigen in Proliferative Colitis of Ferrets". Laboratory Animal Science, vol. 38, No. 1, Feb. 1988, pp. 34-36.

Frey et al., "Coiled bodies contain U7 small nuclear RNA and associate with specific DNA sequences in interphase human cells". Proceedings of the National Academy of Sciences of the United States of America, vol. 92, No. 13, Jun. 1995, pp. 5915-5919.

Gebhart et al., "Cloned DNA Probes Specific for the Intracellular Campylobacter-Like Organism of Porcine Proliferative Enteritis". Journal of Clinical Microbiology, vol. 29, No. 5, May 1991, pp. 1011-1015.

Gebhart et al., "Ileal Symbiont Intracellularis, an Obligate Intracellular Bacterium of Porcine Intestines Showing a Relationship to Desulfovibrio Species". International Journal of Systematic Bacteriology, vol. 43, No. 3, Jul. 1993, pp. 533-538.

Gebhart et al., "Species-specific DNA probes for Campylobacter species isolated from pigs with proliferative enteritis". Veterinary Microbiology, vol. 24, 1990, pp. 367-379.

Griffiths, B., "Scaling-up of Animal Cell Cultures". Animal Cell Culture-A Practical Approach, Chapter 3, IRL Press Limited, Oxford, England, 1986, pp. 33-69.

Guedes et al., "Validation of an immunoperoxidase monolayer assay as a serologic test for porcine proliferative enteropathy". Journal of Veterinary Diagnostic Investigation, vol. 14, 2002, pp. 528-530.

Hancock et al., Modern Microbiological Methods, Bacterial Cell Surface Techniques, A Wiley-Interscience Publication, John Wiley & Sons, Chichester, 1988, pp. 90-91.

Harvey, Stewart C., "Drug Absorption, Action and Disposition". Remington's Pharmaceutical Sciences, 18th Edition, (Ed) Gennaro AR, Mack Publishing Company, Easton, Pennsylvania, 1990, pp. 697-702.

Holyoake et al., "Enzyme-linked immunosorbent assay for measuring ileal symbiont intracellularis-specific immunoglobulin G response in sera of pigs". Journal of Clinical Microbiology, vol. 32, No. 8, 1994, pp. 1980-1985.

Horin et al., "Polymorphisms in equine immune response genes and their associations with infections". Mammalian Genome, vol. 15, 2004, pp. 843-850.

Jasni et al., "Reproduction of proliferative enteritis in hamsters with a pure culture of porcine ileal symbiont intracellularis". Veterinary Microbiology, vol. 41, 1994, pp. 1-9.

Jones et al., "Enhanced Detection of Intracellular Organism of Swine Proliferative Enteritis, Ileal Symbiont Intracellularis, in Feces by Polymerase Chain Reaction". Journal of Clinical Microbiology, vol. 31, No. 10, Oct. 1993, pp. 2611-2615.

Jones, Gary F., "The Diagnosis and Cause of Swine Proliferative Enteritis"., A Thesis Submitted to the Faculty of the Graduate School of the University of Minnesota, Minneapolis, MN, Jun. 1993, pp. 1-190.

Kesl et al., "Tylan® Premix and Enterisole® Li Ileitis vaccine evaluations in a Lawsonia intracellularis challenge model". American Swine Association of Swine Veterinarians, 2004, pp. 139-142.

Knittel et al., "Evaluation of antemortem polymerase chain reaction and serologic methods for detection of Lawsonia intracellularis-exposed pigs". American Journal of Veterinary Research, vol. 59, No. 6, Jun. 1998, pp. 722-723, 725.

Koyama et al., "In Vitro Cultivation and Partial Characterization of Lawsonia Intracellularis from a Japanese Field Case of Porcine Proliferative Enteropathy". Proceedings of the 18th IPVS Congress, vol. 1, Hamburg, Germany, 2004, p. 307.

Kroll et al., "Efficacy of an Avirulent Lawsonia intracellularis Vaccine in Swine". Abstracts of the General Meeting of the American Society for Microbiology, vol. 101, Session No. 236/Z, Abstract Z-40, American Society for Microbiology 101st General Meeting, Orlando, FL, May 23, 2001, p. 747.

Kroll et al., "Lipopolysaccharide-Based Enzyme-Linked Immunosorbent Assay for Experimental Use in Detection of Antibodies to Lawsonia intracellularis in Pigs". Clinical and Diagnostic Laboratory Immunology, vol. 12, No. 6, Jun. 2005, pp. 693-699.

Kuan et al., "Production of Monoclonal Antibody That Recognizes the Lipopolysaccharide of a Campylobacter-Like Organism". Microbiology and Immunology, vol. 36, No. 8, 1992, pp. 791-801.

Lavoie et al., "Equine proliferative enteropathy: a cause of weight loss, colic, diarrhoea and hypoproteinaemia in foals on three breeding farms in Canada". Equine Veterinary Journal, vol. 32, No. 5, Sept. 200, pp. 418-425, Abstract Only.

Lawson et al., "Attempts to Cultivate the Campylobacter-like Organism of the Proliferative Enteropathies". Association of Vet. Teachers and Research Workers, Apr. 1990, Abstract C50.

Lawson et al., "Infection of cultured rat enterocytes by Ileal symbiont intracellularis depends on host cell function and actin polymerisation". Veterinary Microbiology, vol. 45, 1995, pp. 339-350.

Lawson et al., "Intestinal Adenomatosis in the Pig: A Bacteriological Study"., Research Journal of Veterinary Sciences, vol. 37, 1974, pp. 331-336.

Lawson et al., "Intracellular Bacteria of Porcine Proliferative Enteropathy: Cultivation and Maintenance In Vitro". Journal of Clinical Microbiology, vol. 31, No. 5, May 1993, pp. 1136-1142.

Lawson et al., "Proliferative Haemorrhagic enteropathy". Research in Veterinary Science, vol. 27, 1979, pp. 46-51.

Lawson et al., "Review: Proliferative Enteropathy". Journal of Comparative Pathology, vol. 122, 2000, pp. 77-100.

Lomax et al., "Experimentally induced porcine proliferative enteritis in specific-pathogen-free pigs". American Journal of Veterinary Research, vol. 43, No. 9, Sep. 1982, pp. 1615-1621.

Lomax, L.G., "Porcine proliferative enteritis—characterization of the naturally occurring and experimental disease". A Dissertation Submitted to the Graduate Faculty in Partial Fulfillment of the Requirements for the Degree of Doctor of Philosophy. Iowa State Univeristy, Ames, Iowa, 1981, pp. 1-206.

Love et al., "Pathology of Proliferative Haemorrhagic Enteropathy in Pigs". Veterinary Pathology, vol. 16, 1979, pp. 41-48.

McCluskey et al., "LsaA, an Antigen Involved in Cell Attachment and Invasion, Is Expressed by Lawsonia intracellularis during Infection In Vitro and In Vivo". Infection and Immunity, vol. 70, No. 6, Jun. 2002, pp. 2899-2907.

Mcorist et al., "Antimicrobial Susceptibility of Ileal Symbiont Intracellularis Isolated from Pigs with Proliferative Enteropathy". Journal of Clinical Microbiology, vol. 33, No. 5, May 1995, pp. 1314-1317.

Mcorist et al., "Characterization of Lawsonia intracellularis gen. nov., sp. nov., the Obligately Intracellular Bacterium of Porcine Proliferative Enteropathy". International Journal of Systematic Bacteriology, vol. 45, No. 4, Oct. 1995, pp. 820-825.

Mcorist et al., "Control of porcine proliferative enteropathy by oral administration of chlortetracycline". The Veterinary Record, vol. 144, Jan. 1999, pp. 48-49.

Mcorist et al., "Early Lesions of Proliferative Enteritis in Pigs and Hamsters". Veterinary Pathology, vol. 26, No. 3, May 1989, pp. 260-264.

Mcorist et al., "Entry of the bacterium ileal symbiont intracellularis into cultured enterocytes and its subsequent release". Research in Veterinary Science, vol. 59, 1995, pp. 255-260.

\* cited by examiner

LAWSONIA VACCINE AND METHODS OF USE THEREOF

RELATED APPLICATION

This application claims the benefit of U.S. Provisional Patent Application Ser. No. 60/699,946, filed on Jul. 15, 2005, the teachings and contents of which are incorporated by reference herein.

BACKGROUND OF THE INVENTION

1. Field of the Invention

The present invention is broadly concerned with improved vaccination methods for immunization against porcine proliferative enteritis, known as ileitis, which is caused by an obligate intracellular bacterium *Lawsonia intracellularis* (*Lawsonia* or *L. intracellularis*). Specifically, the invention provides methods for providing increased protection against *L. intracellularis* by vaccinating pregnant sows; by vaccinating pregnant sows and then subsequently vaccinating their young piglets within about three weeks after birth; and by vaccinating young piglets within 25 or 26 days of birth, respectively.

2. Description of the Prior Art

Porcine proliferative enteritis (PPE), is a naturally occurring disease that can affect pigs from weaning to young adult stage. It has been established that the causative agent is *Lawsonia intracellularis*, an obligate intracellular, gram-negative bacterium which cannot be cultured by normal bacteriological methods on conventional cell-free media and has been thought to require cells for growth. S. McOrist et al., Infection and Immunity, Vol. 61, No. 19, 4286-4292 (1993) and G. Lawson et al., J. of Clinical Microbiology, Vol. 31, No. 5, 1136-1142 (1993) discuss cultivation of *L. intracellularis* using IEC-18 rat intestinal epithelial cell monolayers in conventional tissue culture flasks. In U.S. Pat. Nos. 5,714,375 and 5,885,823, both of which patents are herein incorporated by reference in their entireties, cultivation of *L. intracellularis* in suspended host cells was described.

Pathogenic and non-pathogenic attenuated bacteria strains of *L. intracellularis* are well known in state of the art. For example, WO 96/39629 and WO 05/011731 describe non-pathogenic attenuated strains of *L. intracellularis*. Further attenuated bacteria strains of *L. intracellularis* are known from WO 02/26250 and WO 03/00665. The teachings and content of each of these references are incorporated by reference herein.

The disease is first characterized by its gross and microscopic pathology, and later by the demonstration of the intracellular bacteria within affected cells. The characterizing pathological feature of the disease is the proliferation of immature epithelial cells in the crypts of the ileum (terminal part of the small intestine), the large intestine or both. Sections of infected tissue are characterized by a reddened thickening mucosa resembling a "garden hose," and enteric lesions. The gut thickening ultimately prevents normal gut function, absorption capabilities, and nutrient transfer. Clinical effects of the disease are chronic weight loss, unthriftiness, diarrhea, and death. The disease is of economic importance owing to death loss, increased medication costs, poor weight gain and decreased food conversion in affected animals. Clinical cases of ileitis are observed, most notably in pigs 6-20 weeks of age. However, the presence of *L. intracellularis* has been confirmed (by PCR) in recently weaned pigs (3-4 weeks of age), suggesting *L. intracellularis* exposure occurs in the nursery and perhaps, originates from *Lawsonia*-positive dams (Mauch and Bilkei (2004) Vet Rec 155: 532; Marsteller et al. (2003). Swine Health Prod 11:127-130; Stege et al. (2004). Vet Micro 104: 197-206). These observations underline the importance for incorporating prevention strategies such as vaccination earlier in the production system.

Current vaccination strategies for immunization against ileitis involve oral administration of the vaccine to *Lawsonia*-naïve pigs from only three weeks of age and older, because piglets below this age group could have maternal antibodies positive for *L. intracellularis* due to previous sow exposure or vaccination. Prior to the method of the present invention it was believed that the presence of maternal antibodies or other lactogenic factors could potentially interfere with the efficacy of vaccinations in such piglets, because the maternal antibodies have the ability to neutralize the vaccine before the piglet's immune system can recognize it and begin secreting its own antibodies. Therefore, vaccination of young piglets has been avoided in the face of maternal immunity.

SUMMARY OF THE INVENTION

The present invention overcomes deficiencies of the prior art and provides novel methods for providing increased swine protection against ileitis. In particular, the present invention provides a method of administering an immunologically effective amount of vaccine to sows, and/or young piglets within weeks after birth, in order to immunize them against ileitis. It was discovered that the transfer of maternal immunity from a *Lawsonia*-vaccinated or exposed sow to piglet provides some protection against ileitis in piglets for at least 6 weeks after birth. Unless vaccinated however, they quickly become susceptible to the disease. The methods of the present invention demonstrated that use of the vaccine in pregnant animals at high doses, after repeated doses, and even when administered during the second or third stages of gestation was surprisingly safe and effective for providing maternal immunity.

Thus the present invention generally relates to a method for the vaccination of pregnant animals (preferably pigs) against *L. intracellularis* infections, wherein said pregnant animals are vaccinated with *L. intracellularis* antigen. According to a further aspect, the vaccination is with high doses and/or repeated doses of *L. intracellularis* antigen. According to another aspect, the present invention relates to a method for the vaccination of pregnant animals (preferably pigs) against *L. intracellularis* infections, wherein said pregnant animals are vaccinated during the second or third stages of gestation, preferably those pregnant animals are vaccinated with high doses and/or repeated doses of *L. intracellularis* antigen.

In a preferred embodiment, there is provided a method of vaccinating pigs against ileitis by administering a *Lawsonia* vaccine to a pregnant sow at least one time before farrowing, preferably two times before farrowing and most preferably three times prior to farrowing ("repeated doses"). In some forms, the pregnant sows are vaccinated with high doses of the *L. intracellularis* antigen. When the vaccine is administered to the sow three times, the first administration should occur between 50 and 60 days before farrowing, preferably between 52 and 58 days before farrowing, and most preferably between 54 and 56 days before farrowing. The second administration should occur between 30 and 40 days before farrowing, preferably between 32 and 38 days before farrowing, and most preferably between 34 and 36 days before farrowing. The final administration should occur between 10 and 20 days before farrowing, preferably between 12 and 18 days before farrowing, and most preferably between 14 and 16 days before farrowing. After the sow gives birth, the vaccine is then administered to each of the piglets, after they are weaned up until slaughter, but preferably before they reach three weeks of age, in any case, at least within 10 to 25 and 26 days of age, respectively (preferably between 16 to 26 days of age), more preferably between 10 to 21 days of age, even more preferably between 15 to 21 days of age, and most preferably between 19 and 21 days of age. In another embodiment of this method, the vaccine is administered to each of the piglets before 26 days of age, preferably between 16 to 26 days of age, more preferably between 18 to 24 days of age, still more preferably between 19 to 22 days of age, and most preferably at 21 days of age.

Thus, in yet another embodiment, the present invention provides a method for vaccinating pregnant sows as well as the farrowed piglets. Preferably, the pregnant sows and farrowed piglets are vaccinated as described above.

It was further discovered that maternal immunity, unexpectedly, does not interfere with successful vaccination of the piglets shortly after birth, and in fact, piglets vaccinated within about three weeks after birth, as described herein, have reduced gross pathology associated with the disease compared to non-vaccinated piglets.

Thus the present invention relates to a method for the vaccination of young animals (preferably young piglets) within about three weeks after birth against *L. intracellularis* infections. Preferably, those young animals (preferably young piglets) are vaccinated within days 21 days of age. Even more preferably, those young animals (preferably young piglets) are vaccinated within days 10 to 25 and 26, respectively of age. Even more preferably, those young animals (preferably young piglets) are vaccinated within days 10 to 21 of age. Even more preferably, those young animals (preferably young piglets) are vaccinated within days 12 to 21, respectively of age. Even more preferably, those young animals (preferably young piglets) are vaccinated within days 15 to 21 of age, most preferably within days 19 to 21 of age. In another embodiment of this method, the vaccine is administered to each of the piglets before 26 days of age, preferably between 16 to 26 days of age, more preferably between 18 to 24 days of age, still more preferably between 19 to 22 days of age, and most preferably at 21 days of age. The vaccine for use in accordance with the present invention can be any vaccine which provides protection against *L. intracellularis*. Preferably, the vaccine is a live virus *L. intracellularis* vaccine. More preferably, the vaccine is Enterisol® Ileitis B3903 (Boehringer Ingelheim Vetmedica, Inc.).

The vaccine is administered to animals, preferably mammals, and still more preferably pigs, in any conventional manner, most preferably through oral drench.

The dosage to be administered will depend upon the particular case, but in any event, it is the amount sufficient to induce a protective antibody and/or cell-mediated immune response against ileitis. Proper dosage is determinable by means known in the art without undue experimentation, and will most often be contingent upon the particular vaccine utilized. In many cases, a suitable dosage ranges from 0.1 ml to 10 ml, and preferably from about 1 ml to 5 ml. In the case of Enterisol® Ileitis, the dosage is preferably at least 2 ml per pig. Dosages can also be calculated on a dry weight basis per weight of the pig for non-aqueous vaccinations.

The studies set forth in the examples below were conducted to evaluate vaccine efficacy in pigs derived from *Lawsonia intracellularis*-exposed and *Lawsonia*-negative sows. Furthermore, the studies evaluated whether there was any maternal interference resulting from vaccination of piglets at three weeks of age.

DETAILED DESCRIPTION OF THE INVENTION

The term "vaccination" or "vaccinating" as used herein means, but is not limited to, a process which includes the administration of an *L. intracellularis* antigen to an animal, wherein said *L. intracellularis* antigen, when administered to said animal elicits or is able to elicit an immune response in said animal against *L. intracellularis*.

The term "animal" as used herein, means but is not limited to, birds, fish, and mammals such as cattle, pigs, horses, and primates. However, according to one preferred embodiment of the present invention, the animal is a pig, preferably a piglet between 10 to 25 and 26 days of age, respectively, preferably between 10 to 21 days of age, even more preferably between 15 to 21 days of age, and most preferably between 19 and 21 days of age. In another preferred embodiment, the piglet is less than 26 days of age, preferably between 16 to 26 days of age, more preferably between 18 to 24 days of age, still more preferably between 19 to 22 days of age, and most preferably 21 days of age.

The term "an effective dose" or "efficacious dose" as used herein means, but is not limited to, an amount of antigen that elicits or is able to elicit an immune response in an animal, to which said effective dose of *L. intracellularis* antigen is administered.

An "immunological or immune response" to a composition or vaccine is the development in the host of a cellular and/or antibody-mediated immune response to the composition or vaccine of interest. Thus, the term "elicits or is able to elicit an immune response" means, but is not limited to an immunological process in a host characterized in that said host develops a cellular and/or antibody-mediated immune response to the composition or vaccine of interest. Usually, an "immune response" includes but is not limited to one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction, including a reduction in severity, or lack of the symptoms associated with host infections as described above.

The amount of antigen that is effective to elicit an immune response or is able to elicit an immune response in an animal depends on the ingredients of the vaccine and the schedule of administration. Typically, when killed bacterial antigen is used in the vaccine, the vaccine contains an amount of about $10^3$ to about $10^9$ of the bacterium per dose, preferably, about $10^4$ to about $10^8$ of the bacterium per dose, and still more preferably about $10^5$ to about $10^6$ bacterium per dose.

In particular, when modified live *L. intracellularis* bacteria are used in the vaccines, e.g. the bacteria isolates designated isolate B3903, ATCC accession No. PTA-4926 and designated isolate N34NP40wk, ATCC accession No. 55783 (both described in WO 96/39629 and WO 05/011731), the recommended dose to be administered to the susceptible animal is preferably about 3.0 $TCID_{50}$ (tissue culture infective dose 50% end point)/dose to about 6.0 $TCID_{50}$/dose and more preferably about 4.0 $TCID_{50}$/dose to about 5.0 $TCID_{50}$/dose. In a preferred embodiment, the titer of the vaccine is about 4.9 $TCID_{50}$/dose as determined by Tissue Culture Infective Dose 50% endpoint dilution assay ($TCID_{50}$).

Sub-unit vaccines are normally administered with an antigen inclusion level of at least 0.2 µg antigen per dose, preferably with about 0.2 to about 400 µg/dose, still more preferably with about 0.3 to about 200 µg/dose, even more preferably with about 0.35 to about 100 µg/dose, still more preferably with about 0.4 to about 50 µg/dose, still more preferably with about 0.45 to about 30 µg/dose, still more preferably with about 0.6 to about 15 µg/dose, even more preferably with about 0.75 to about 8 µg/dose, even more preferably with about 1.0 to about 6 µg/dose, and still more preferably with about 1.3 to about 3.0 µg/dose.

In general, the quantity of antigen will be between 5 and 5000 micrograms, and between $10^{2.0}$ and $10^{9.0}$ $TCID_{50}$, preferably between $10^{3.0}$ and $10^{6.0}$ $TCID_{50}$, and more preferably between $10^{4.0}$ and $10^{5.0}$ $TCID_{50}$, when purified bacteria are used.

As used herein, the term "high doses" means in general at least the three-fold amount of antigen of a single dose normally used for the vaccination of adult animals. In particular, the term "high doses" means in respect to live modified L. intracellularis an amount of at least $3 \times 10^{3.0}$ to $3 \times 10^{9.0}$ $TCID_{50}$, preferably about $3 \times 10^{4.5}$ to $3 \times 10^{6.0}$ $TCID_{50}$. In particular, the term "high doses" means in respect to killed L. intracellularis antigen an amount of at least $3 \times 10^{4.0}$ to $3 \times 10^{9.0}$ organisms or bacteria, preferably about $3 \times 10^{6.0}$ to $3 \times 10^{8.0}$ organisms or bacteria. In particular, the term "high doses" means in respect to any sub-unit L. intracellularis antigen an amount of at least 3×0.2 to about 3×400 (0.6 to about 1200) µg/dose. In this application, high doses of L. intracellularis antigen was administered to pregnant sows in order to induce a heightened immunological response in the pregnant sow that would be transmitted to the offspring and provide some level of immunity to the farrowed piglets.

As used herein, the term "repeated doses" means the administration of the L. intracellularis antigen of a least two times, preferably of three times. Examples for a "repeated doses" vaccination regime for pregnant sows are given above.

As used herein the term "increased protection" means, but is not limited to, a statistically significant reduction in severity or frequency of one or more clinical symptoms and/or lesion development which are associated with L. intracellularis infections (e.g. frequency of cross lesions determined by the method and according to the criteria defined in Example 1, etc.) in a vaccinated group of animals vs. a non-vaccinated control group of animals. The term "statistically significant reduction of clinical symptoms" means but is not limited to, that the frequency in the incidence of at least one clinical symptom and/or lesion development in the vaccinated group of animals is at least 20%, preferably 30%, even more preferably 40%, still more preferably 50%, even more preferably 60%, still more preferably 70%, even more preferably 80%, still more preferably 90%, and most preferably 95% lower than in the non-vaccinated control group after the challenge with an infectious L. intracellularis bacteria.

As used herein, the term "L. intracellularis" or "Lawsonia" means the intracellular, curved gram-negative bacteria described in detail by C. Gebhart et al., Int'l. J. of Systemic Bacteriology, Vol. 43, No. 3, 533-538 (1993) and S. McOrist et al., Int'l. J. of Systemic Bacteriology, Vol. 45, No. 4, 820-825 (1995), each of which is incorporated herein by reference in their entireties, and includes but is not limited to the isolates described in WO 96/39629 and WO 05/011731. In particular, the term "L. intracellularis" also means, but is not limited to the isolates deposited under the Budapest Treaty with the American Type Culture Collection, 10801 University Boulevard, Manassas, Va. 20110-2209 and assigned ATCC accession number PTA 4926 or ATCC accession number 55783. Both isolates are described in WO 96/39629 and WO 05/011731, respectively. The term "L. intracellularis" also means, but is not limited to any other L. intracellularis bacteria strain, or isolate, preferably having the immunogenic properties of at least one of the L. intracellularis strains described in WO 96/39629 and WO 05/011731, in particular having the immunogenic properties of at least one of the isolates deposited under the Budapest Treaty with the American Type Culture Collection, 10801 University Boulevard, Manassas, Va. 20110-2209 and assigned ATCC accession number PTA 4926 or ATCC accession number 55783.

A strain or isolate has the "immunogenic properties" of at least one of the L. intracellularis strains described in WO 96/39629 and WO 05/011731, in particular, of the isolates deposited as ATCC accession number PTA 4926 or ATCC accession number 55783, when it is detectable at least with one of the anti-L. intracellularis specific antibodies, described in WO06/01294, in an detection assay that is also described in WO06/01294. Preferably those antibodies are selected from the antibodies having the reference numbers 301:39, 287:6, 268:29, 110:9, 113:2 and 268:18. Preferably, the detection assay is a sandwich ELISA as described in Examples 2 and 3 of WO06/12949, whereas antibody 110:9 is used as a capture antibody and antibody 268:29 is used as conjugated antibody. All antibodies disclosed in WO06/12949 are produced by hybridoma cells, which are deposited at the Centre for Applied Microbiology and Research (CAMR) and European Collection of Cell Cultures (ECACC) ", Salisbury, Wiltshire SP4 0JG, UK, as a patent deposit according to the Budapest Treaty. The date of deposit was May 11, 2004. HYBRIDOMA CELL LINE 110:9 is successfully deposited under ECACC Acc. No. 04092204. HYBRIDOMA CELL LINE 113:2 is successfully deposited under ECACC Acc. No. 04092201. HYBRIDOMA CELL LINE 268:18 is successfully deposited under ECACC Acc. No. 04092202. HYBRIDOMA CELL LINE 268:29 is successfully deposited under ECACC Acc. No. 04092206. HYBRIDOMA CELL LINE 287:6 is successfully deposited under ECACC Acc. No. 04092203. HYBRIDOMA CELL LINE 301:39 is successfully deposited under ECACC Acc. No. 04092205.

The term "L. intracellularis antigen" as used herein means, but is not limited to, any composition of matter that comprises at least one antigen that can induce, stimulate or enhance the immune response against a L. intracellularis-caused infection, when administered to an animal. Preferably, said L. intracellularis antigen is a complete L. intracellularis bacterium, in particular in an inactivated form (a so-called killed bacterium), a modified live or attenuated L. intracellularis bacterium (a so-called MLB), any sub-unit, polypeptide or component of L. intracellularis, or any chimeric vector, when each comprises at least an immunogenic amino acid sequence of L. intracellularis. The terms "immunogenic protein", "immunogenic polypeptide" or "immunogenic amino acid sequence" as used herein refer to any amino acid sequence which elicits an immune response in a host against a pathogen comprising said immunogenic protein, immunogenic polypeptide or immunogenic amino acid sequence. In particular, an "immunogenic protein", "immunogenic polypeptide" or "immunogenic amino acid sequence" of L. intracellularis means any amino acid sequence that codes for an antigen which elicits an immunological response against L. intracellularis in a host to which said "immunogenic protein", "immunogenic polypeptide" or "immunogenic amino acid sequence" is administered.

An "immunogenic protein", "immunogenic polypeptide" or "immunogenic amino acid sequence" as used herein, includes but is not limited to, the full-length sequence of any proteins, analogs thereof, or immunogenic fragments thereof.

The term "immunogenic fragment" means a fragment of a protein which includes one or more epitopes and thus elicits the immunological response against the relevant pathogen. Such fragments can be identified using any number of epitope mapping techniques that are well known in the art. See, e.g., Epitope Mapping Protocols in Methods in Molecular Biology, Vol. 66 (Glenn E. Morris, Ed., 1996) Humana Press, Totowa, N.J. (The teachings and content of which are incorporated by reference herein.) For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; and Geysen et al. (1986) Molec. Immunol. 23:709-715. (The teachings and content of which are incorporated by reference herein.) Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are incorporated by reference herein.)

Suitable *L. intracellularis* antigens include, but are not limited to those described in EP 1219711; U.S. Pat. No. 6,605,696; WO 96/39629; WO97/20050; WO 00/69903; WO 00/69904; WO 00/69905; WO 00/69906; WO 02/38594; WO 02/26250; WO 03/006665; WO 04/033631; WO 05/026200; and WO 05/011731.

Thus vaccine for use in accordance with the present invention includes any *L. intracellularis* antigen as described above which elicits or is able to elicit an immune response against *L. intracellularis*. Preferably, said vaccine provides at least increased protection against *L. intracellularis*.

Thus according to a further aspect, the present invention relates to a method of vaccinating a young animal against *L. intracellularis* infections comprising the step administering to said young animal within about 3 weeks of age an effective dose of *L. intracellularis* antigen, wherein the *L. intracellularis* antigen is selected from the group consisting of live modified *L. intracellularis* bacteria, killed *L. intracellularis* bacteria or one or more sub-units of *L. intracellularis* bacteria. As mentioned above for one embodiment, preferably the vaccination occurs between day 10 and day 26 of age, more preferably between day 12 and day 21 of age, even more preferably between day 15 to day 21 of age, and most preferably between day 19 to day 21 of age. For another embodiment, vaccination preferably occurs before 26 days of age, preferably between 16 to 26 days of age, more preferably between 18 to 24 days of age, still more preferably between 19 to 22 days of age, and most preferably at 21 days of age.

Preferably, the vaccine comprises modified live *L. intracellularis* bacteria. More preferably, the vaccine is Enterisol® Ileitis B3903 (Boehringer Ingelheim Vetmedica, Inc.).

According to a further aspect, the present invention relates to a method of vaccinating a young animal preferably a young piglet, against *L. intracellularis* infections comprising the step administering to said young animal starting between day 10 and day 26 of age, more preferably between day 12 and day 21 of age, even more preferably between day 15 to day 21 of age, and most preferably between day 19 to day 21 of age, or the young animal before 26 days of age, preferably between 16 to 26 days of age, more preferably between 18 to 24 days of age, still more preferably between 19 to 22 days of age, and most preferably at 21 days of age, a dose of about 3.0 $TCID_{50}$ to about 6.0 $TCID_{50}$ of the live modified *L. intracellularis* bacteria. Preferably, said bacteria is that included in the vaccine Enterisol® Ileitis B3903 (Boehringer Ingelheim Vetmedica, Inc.).

According to a further aspect, the present invention relates to a method of vaccinating a young animal, preferably a young piglet, against *L. intracellularis* infections comprising the step administering to said young animal starting between day 10 and day 26 of age, more preferably between day 12 and day 21 of age, even more preferably between day 15 to day 21 of age, and most preferably between day 19 to day 21 of age, or before 26 days of age, preferably between 16 to 26 days of age, more preferably between 18 to 24 days of age, still more preferably between 19 to 22 days of age, and most preferably at 21 days of age, an effective dose of *L. intracellularis* antigen, wherein the young animal is *L. intracelluaris* and anti-*L. intracellularis* maternal antibody negative.

According to a further aspect, the present invention also relates to new medicinal use of an effective amount of *L. intracellularis* antigen for the preparation of medicament, preferably a vaccine composition, for the vaccination of a young animal, preferably a young piglet, between day 10 and day 26 of age, more preferably between day 12 and day 21 of age, even more preferably between day 15 to day 21 of age, and most preferably between day 19 to day 21 of age, or before 26 days of age, preferably between 16 to 26 days of age, more preferably between 18 to 24 days of age, still more preferably between 19 to 22 days of age, and most preferably at 21 days of age.

According to a further aspect of said medicinal use described above, the *L. intracellularis* antigen is selected from the group consisting of live modified *L. intracellularis* bacteria, killed *L. intracellularis* bacteria or one or more sub-units of *L. intracellularis* bacteria. Preferably, the *L. intracellularis* antigen is live modified *L. intracellularis* bacteria. More preferably, said young animal is administered with a dose of about 3.0 $TCID_{50}$ to about 6.0 $TCID_{50}$ of the live modified *L. intracellularis* bacteria. The manufacture of vaccine compositions comprising a *L. intracellularis* antigen are conventional in the state of the art and known to a skilled artisan. For example the skilled person in the art is able to know additional components which may be comprised in said composition (see also Remington's Pharmaceutical Sciences. (1990). 18th ed. Mack Publ., Easton). The expert may use known injectable, physiologically acceptable sterile solutions. For preparing a ready-to-use solution for parenteral injection or infusion, aqueous isotonic solutions, such as e.g. saline or corresponding plasma protein solutions, are readily available. The vaccine compositions may be present as lyophylisates or dry preparations, which can be reconstituted with a known injectable solution directly before use under sterile conditions, e.g. as a kit of parts.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like.

"Diluents" can include water, saline, dextrose, ethanol, glycerol, and the like. Isotonic agents can include sodium chloride, dextrose, mannitol, sorbitol, and lactose, among others. Stabilizers include albumin and alkalisalts of ethylendiamintetracetic acid, among others.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, or water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997). (The teachings and content of which are hereby incorporated by reference.) For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book. (The teachings and content of which are hereby incorporated by reference.)

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated. Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, among many others.

Preferably, the adjuvant is added in an amount of about 100 µg to about 10 mg per dose. Even more preferably, the adjuvant is added in an amount of about 100 µg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

The vaccine composition can further include one or more other immunomodulatory agents such as, e.g., interleukins, interferons, or other cytokines. The vaccine compositions can also include Gentamicin and Merthiolate. While the amounts and concentrations of adjuvants and additives useful in the context of the present invention can readily be determined by the skilled artisan, the present invention contemplates compositions comprising from about 50 µg to about 2000 µg of adjuvant and preferably about 250 µg/ml dose of the vaccine composition. In another preferred embodiment, the present invention contemplates vaccine compositions comprising from about 1 µg/ml to about 60 µg/ml of antibiotics, and more preferably less than about 30 µg/ml of antibiotics.

The vaccine is administered to animals, preferably mammals, and still more preferably pigs, in any conventional manner, most preferably through oral drench. The dosage to be administered will depend upon the particular case, but in any event, it is the amount sufficient to induce a protective antibody or cell-mediated immune response against ileitis.

According to a further aspect of the invention, the L. intracellularis vaccines used for the vaccination of the young animals (preferably the young piglets) are administered in one or repeated doses. Live or killed vaccine may be administered 1 or 2 times at 2 to 4 week intervals after the initial vaccination. For the attenuated, live vaccines, one dose is preferred. Preferably, the first or single administration is performed at day 16 to day 26 of age, more preferably at day 18 to day 24 of age, even more preferably at day 19 to day 22 of age, and most preferably at day 21 of age, as described above, or starting between day 10 and day 26 of age, more preferably between day 12 and day 21 of age, even more preferably between day 15 to day 21 of age, and most preferably between day 19 to day 21 of age.

If a second administration is desirable or necessary, the second administration is performed about 1 to about 4 weeks after the first administration of the vaccine. According to a further aspect, revaccination is performed in an interval of 3 to 12 months after administration of any previous vaccination. Administration of subsequent vaccine doses is preferably done on a 6 month to an annual basis.

EXAMPLES

The following examples are representative of preferred embodiments of the present invention. It is understood that nothing herein should be taken as a limitation upon the overall scope of the invention.

Example 1

This example evaluated the efficacy of a Lawsonia vaccine in three-week old piglets born from Lawsonia-vaccinated and non-vaccinated sows and determined whether or not sow vaccination caused maternal immune interference that prevented a response to piglet vaccination, as measured by a reduction in the induction in disease following virulent pure culture challenge of both vaccinated and non-vaccinated piglets. The primary study parameters used to measure efficacy were macroscopic and microscopic lesions of the ileum and colon. Additionally, this example evaluated the Lawsonia vaccine for safety issues when administered to pregnant sows during the second and third stages of gestation following single and repeated dose administration.

Materials and Methods

In a blinded study, sixteen healthy, pregnant, and *Lawsonia* sero-negative sows were obtained and randomly divided into 2 groups, A and B, each having 8 sows. Group A received 3 doses of Enterisol Ileitis B3903 by oral drench on days −55, −35, and −14, in an attempt to induce a high level of maternal immunity prior to farrowing. Group B sows received a placebo prior to farrowing and served as negative controls. Sows were first fed a non-medicated, commercial gestation ration prior to being switched to a non-medicated lactation diet. Efforts were made to have uniform conception and farrowing by all of the sows, however, there was some variation (10 days) in the timing of farrowing. In order to prevent the variability problems associated with having multiple vaccination and challenge days, the middle of the farrowing dates was established as day 0 of the trial. All piglets used in the vaccine and challenge portion of the study were 21±5 days of age at the time of vaccination (Day 21). Piglets were first fed a non-medicated starter ration, followed by a non-medicated nursery ration, followed by a non-medicated grow-finish ration. The serology samples which were collected from pigs were collected on the actual day of birth, 7 days of age, and 14 days of age, to insure accurate measurement of maternal antibody, if present. Serology was taken from sows prior to farrowing. Additionally, sows were necropsied on day 22, their ileum and colon tissues were evaluated for gross pathology, their ileum, colon, mesenteric lymph nodes, and tonsils were evaluated by PCR, stillborn pigs were tested by PCR, and reproductive litter performance of the sows was evaluated by recording pigs as live-born, stillborn, or mummies on the day of farrowing.

After farrowing (at day 21 of the study), 100 healthy piglets were blocked by litter and then randomly assigned to one of six treatment groups, each of which was housed separately throughout the study. Piglets derived from vaccinated sows (Group A) were randomly assigned to treatment groups 1-3. Piglets from non-vaccinated sows (Group B) were randomly assigned to treatment groups 4-6. On day 21, treatment groups 1 and 4, each having 20 piglets per group, received a 2 ml dose ($1 \times 10^{5.0}$ $\log_{10}$ $TCID_{50}$/dose) of Enterisol Ileitis B3903 vaccine by direct oral drench. Treatment groups 2 and 5, each having 20 piglets per group, received one 2 ml dose placebo by direct oral drench. Treatment groups 3 and 6, each having 10 piglets per group, received no treatment and served as strict controls to validate the susceptibility of the pig source to *Lawsonia* infection.

Three weeks after vaccination (day 42 of the study), test piglets in treatment groups 1, 2, 4 and 5 were challenged by receiving one 10 ml dose ($1 \times 10^{7.3}$ $\log_{10}$ $TCID_{50}$/dose) of virulent low-passage pure culture *Lawsonia* heterologous isolate N101494 . . . by gastric gavage. However, any other infectious wild-type or low passaged *L. intracellularis* isolate can be used as challenge bacteria. On day 63 of the study (three weeks post-challenge), all treatment groups (1-6) were euthanized and necropsied for gross and microscopic lesion analysis for PPE.

The primary criterion used to determine the efficacy of the Enterisol Ileitis B3903 vaccine in piglets against a heterologous virulent pure-culture challenge was the observation of lesion development using both macroscopic and microscopic techniques to evaluate lesions in the ileum and colon. Gross lesions were evaluated in sections of the ileum, at the ileal/cecal junction, and in the colon at the time of the termination of the study. Intestinal lesions were graded on their level of severity and additional samples were taken from any infected site of the tissue for PCR, IHC, and H&E analysis. Lesion severity was determined by the degree of mucosal thickening found within the mucosal lining of the ileum. A lesion score of 0 indicated no evidence of mucosal thickening, edema, mucosal ridges/folds, or prominence of serosal reticulation. A lesion score of 1 indicated mild thickening including the presence of small ridges/folds in mucosa, mild edema of the mucosal wall, and in some cases hyperemia. A lesion score of 2 was equated with moderate thickening and/or inflammation. It was evidenced by prominent deep ridges/folds in mucosa, moderate edema of the mucosal wall, reticulation of serosal surfaces, and in some cases, hyperemia. A lesion score of 3 indicated severe thickening and/or inflammation, evidenced by severe and deep ridges/folds in mucosa, moderate edema of the mucosal wall, reticulation of serosal surfaces, and again in some cases, hyperemia. A lesion score of 4 indicated severe thickening and/or inflammation and/or the presence of blood. This lesion score was evidenced by severe and deep ridges/folds in mucosa, moderate edema of the mucosal wall, reticulation of serosal surfaces, again in some cases, hyperemia, and the presence of bloody contents and/or blood clots. Finally, a lesion score of 5 indicated necrosis evidenced by severe lesions of the mucosal surface such that the presence of necrosis is present or in some cases the entire mucosal surface is sloughed or detached due to the severity of the lesion.

Microscopic lesions caused by *Lawsonia* are pathognomic for PPE. Histopathological lesions of the disease include epithelial hyperplasia, especially in the mucosal crypts with a distinct absence of goblet cells. *Lawsonia* is usually found within the proliferating epithelial cells of the mucosal crypt. Sections of ileum approximately 2-4 cm long were placed in buffered formalin for histologic examination using Hematoxylin and Eosin (H&E) and IHC staining methods. H&E stains detect the presence of crypt hyperplasia caused by *Lawsonia* infection while IHC stains exploit the specificity of an anti-*Lawsonia* monoclonal antibody in confirming the presence of the organism and microscopic lesion development in affected tissues. The anti-*Lawsonia* monoclonal antibody specifically detects whole cell *Lawsonia* by targeting an outer membrane protein present in all *Lawsonia* isolates. This monoclonal was derived from the hybridoma cell line VPM53, developed by researchers at the University of Edinburg, Scotland. The presence of *Lawsonia* organisms and microscopic lesion severity as determined by IHC staining of ileal sections were scored with a score of 0 indicating no proliferative enterocytes (lesions), a score of 1 indicating mild, focal lesions, a score of 2 indicating moderate, diffuse lesions, and a score of 3 indicating severe, diffuse lesions. With respect to the presence of organisms, the IHC scoring system scored the presence of no organisms as a 0, the presence of few, focal organisms as a 1, the presence of moderate, diffuse organisms as a 2, and the presence of severe, diffuse organisms as a 3.

The secondary criteria of measurements were the observation of clinical symptoms, detection of *Lawsonia* in fecal swabs and tissues by PCR, the ADWG and seroconversion (IFAT) due to piglet exposure to *Lawsonia*.

Daily health observations were made from the date of the study initiation to the day of challenge for each test animal. Clinical health parameters, including diarrhea, behavior and body condition, were scored daily from the day of challenge (day 42) to the day prior to termination (day 62). The score reflected the severity of illness. For diarrhea, a score of 1 indicated normal feces, a score of 2 indicated semi-solid feces with no blood, a score of 3 indicated watery feces but without any blood or dark feces, and a score of 4 indicated blood-tinged feces, whether they were loose or formed. A behavior score of 1 indicated normal behavior, a score of 2 indicated mild to moderately depressed behavior (will stand alone), and a score of 3 indicated severely depressed or recumbent behavior. A body condition score of 1 indicated a normal body condition, a score of 2 indicated a mild to moderately gaunt body condition, and a score of 3 indicated a severely gaunt body condition.

Fecal shedding of *Lawsonia* was evaluated by Ileitis PCR by testing fecal swabs (f-PCR) on days −55, −35, −14, 21, 28, 35, 42, 49, 56 and 63 of the study. Fecal swabs were tested for the presence of *Lawsonia* DNA in feces using PCR. Fresh tissue sections were retrieved from each test animal at the termination of the study on day 63. Qualitative analysis of bacterial content in tissues was evaluated by Ileitis PCR (t-PCR) along with histological evaluation for *Lawsonia* in the ileum, colon, tonsils and mesenteric lymph node on day 63 of the study. The PCR assay was developed by Jones, et al., and it exploits the specificity of two oligonucleotide primers (20 base pairs each) to produce a 319 bp fragment from *Lawsonia* genomic DNA. These primers target a previously determined sequence of genomic DNA specific for *Lawsonia*. Fragments of DNA produced during PCR are compared to Ileitis-positive and -negative DNA extraction and PCR reaction controls for confirmation of a "positive" or "not positive" result. The positive DNA extraction control is whole-cell *Lawsonia* with infected McCoy cells in 1× Phosphate-Buffered Saline (PBS) (200l/tube). The negative DNA extraction control is uninfected McCoy cells in 1×PBS (200l/tube). Ileitis PCR reaction controls consist of *Lawsonia* genomic DNA purified from cell culture harvest material (*Lawsonia*+ McCoy cells) while the negative control is RNAse free water (Amresco, Solon, Ohio). A test sample positive for Lawsonia DNA will produce the identical size DNA fragment (319 bp) as both Ileitis PCR-positive controls (extraction and reaction) while negative samples will not produce a fragment of this size. Preparations of extracted DNA from each test sample were obtained using ISO-QUICK DNA extraction kits (ORCA Research, Inc., Bothell, Wash.). PCR results were used to determine shedding of *Lawsonia* in piglets vaccinated with Enterisol Ileitis B3903 and/or challenged with the *Lawsonia* heterologous isolate N101494.

Weights were measured on the day of vaccination (day 21), the day of challenge (day 42), and on the day of study termination (day 63) in order to calculate the average daily weight gains (ADWG) of each treatment group. The ADWG for each group were compared with each other for post-vaccination and post-challenge ADWG. Body weights were determined using an electronic weigh bar scale system (Weigh-Tronix, Weigh-Tronix, Inc., Fairmont, Minn.) calibrated using certified test weights prior to and after each use.

Serum was tested using Indirect Fluorescent Antibody Test (IFAT) to detect anti-*Lawsonia* antibodies in test animals. Venous whole blood in vacutainer tubes from sows on days −55, −35, and −14 and in all test animals at 0, 7, and 14 days of age, and on trial days 21, 28, 35, 42, 49, 56, and 63 of the study. The blood was allowed to clot before being centrifuged, and the serum collected and frozen. The IFAT then screened the pig serum for anti-*Lawsonia* IgG molecules. Anti-*Lawsonia* antibodies attach to outer membrane antigens of whole cell *Lawsonia*, completely covering the organism which is fixed to the bottom of each well in a 96-well microtiter plate. And anti-IgG FITC-tagged secondary antibody conjugate was introduced to bind to any IgG-antigen complexes within each well. These FITC-bound complexes illuminate fluorescent green under ultraviolet light. A positive test sample reveals many bright green, small, curved-shaped rods resembling *Lawsonia*, or infected McCoy cells containing numerous *Lawsonia*. A negative IFAT test sample shows a dull (faint) green background of McCoy cells. The results ascertained by the IFAT were used to observe a seroconversion pattern in groups receiving a vaccination and/or virulent challenge indicative of *Lawsonia* exposure in the test animal.

A $TCID_{50}$ endpoint assay was conducted on representative samples of each vaccine dose administered to test piglets on day 21 of this study. Five replicates of representative test samples were diluted ten fold ($10^{-1}$ to $10^{-6}$) pre and post vaccination and challenge administration in Dulbecco's Modified Essential Media fortified with Ham's F12 (DMEM F12) and 5% heat inactivated Newborn Bovine Serum (NBS) (JRH Biosciences, Lenexa, Kans.). Diluted samples were tested to determine the amount of live *Lawsonia* in each test sample. Average titers were calculated from 5 replications pre and post vaccine and pre and post challenge administration and multiplied by the volume of test material given to each piglet to determine the total log10 *Lawsonia* per dose. The total average titers ($log_{10}$ $TCID_{50}$/dose) for vaccination or challenge were determined from the average pre and post (2 titers) titration results.

Treatment group comparisons were made by analyzing the data of ADWG, both post-vaccination and post-challenge, clinical scores, seroconversion rates (IFAT), colonization (t-PCR), fecal shedding (f-PCR), gross lesion, and microscopic lesion development by Imunohistochemistry (IHC).

Three piglets (one from Group 1 and two from Group 5) died after vaccination, but before the termination of the study. The piglet from Group 1 was analyzed for *Lawsonia* infection, but the cause of death was determined to be shock/septicemia due to high levels of *E. coli*. The two piglets from Group 5 that died had severe gross and microscopic lesions typical of *Lawsonia* infection and the presumptive cause of death was due to *Lawsonia*.

Results

Evaluation of the fecal and serum samples collected in this study indicated that no sow in either Group A or Group B had detectable *Lawsonia* in its feces or in the ileum or colon. The Group A sows had 5 of 8 animals with detectable IFAT titers in at least one time point during the study. No sows from Group B had a detectable IFAT titer during the same time period. These data are summarized below in Table 1.

TABLE 1

| | Sow data | | | | |
|---|---|---|---|---|---|
| Sow Treatment | Gross Ileum Lesions | Gross Colon Lesions | Tissue PCR (Ileum/Colon/ MLN/Tonsil) | IFA | Average live born pigs/litter |
| A - Vaccinated | 0/8 | 0/8 | 0/8 | 5/8 | 9.4 |
| B - Non-vaccinated | 0/8 | 0/8 | 0/8 | 0/8 | 7.6 |

All sows were necropsied and evaluated for gross lesions typical of *Lawsonia* infection. However, no sow was positive for gross lesions or T-PCR detection.

Despite the fact that vaccine was administered during both the $2^{nd}$ and $3^{rd}$ trimesters of pregnancy, no abnormal general health observations were recorded for any sow during the clinical trial. Farrowing results between Group A and Group B sows were also very similar with an average of 9.4 and 7.6 live-born piglets in each group, respectively. The Group A sows had and average of 1.8 stillborn pigs per litter and no mummies or farrowing mortalities. The Group B sows had an average of 0.9 stillborn, 0.1 mummies, and 0.1 pigs die at farrowing, per litter. Diagnostic evaluation of these stillborn pigs indicated they were *Lawsonia*-negative and within normal losses associated with reproduction. The serology results were as expected in that non-vaccinated sows remained seronegative and some sero-positive animals were noted in Group A. The Group A sows had higher pigs/litter values in comparison to the non-vaccinated controls. This result indicates that there was no negative effect due to vaccination methods or contents. This data is summarized above in Table 1.

Macroscopic piglet lesion development was determined by evaluating and scoring the ileum and colon of each test animal for gross lesions associated with PPE at the time of the termination of the study. Piglets from Groups 1 and 4 had the lowest ileum scores at 0.16 and 0.15, respectively. These were not significantly different and demonstrate vaccine efficacy in pigs from both vaccinated and non-vaccinated sows. Groups 2 and 5 had ileum lesion scores of 0.85 and 2.35, respectively. These were significantly different (P<0.05) and indicate that sow vaccination did provide some level of maternal protection (Group 2) and that the naïve animals were sensitive to virulent challenge (Group 5). Groups 4 and 5 also had significantly different ileum scores (P<0.05) and confirm efficacy of the vaccine in naïve vaccinated piglets. The ileum scores of Groups 1 and 2 were also significantly different (P<0.05) and confirm that vaccination of pigs in *Lawsonia*-positive sows does provide a significant benefit (P<0.05) beyond maternal immunity. The same trends and significance were also noted for the ilea samples in terms of the percent positive animals (positive/group total). Ileum lesions were found in 80% of the pigs of Group 5. In contrast, less than 16% of the animals of both Groups 1 and 4 had ileum lesions.

With respect to gross lesion scores of the colon and the percentage of positive animals, there was a significant difference (P<0.05) between Group 4 and Group 5. There were no other significant differences between treatment groups. The strict controls (Groups 3 and 6) were negative for gross lesions in the ileum and colon and thereby confirm study validity. Results of this testing are provided below in Table 2.

mesenteric lymph node, terminal ileum, and colon were collected at the termination of the study (day 63) and placed in 10% buffered formalin for IHC analysis. *Lawsonia* was not detected by IHC staining of tonsil sections in any treatment groups at the termination of the study. *Lawsonia* was detected in 2/20 of the mesenteric lymph node samples from group 5. All other mesenteric lymph node samples in all other groups were negative and there was no significant difference between treatment groups relative to mesenteric lymph node testing.

Groups 1 and 4 had microscopic ileum scores of 0.35 and 0.15, respectively, and were not significantly different. Group 5 had the highest microscopic ileum score at 2.42 and was significantly (P<0.05) different than both the Group 2 and 4 treatment groups. This demonstrates that there is some level of maternal immunity in Group 2 and that the vaccine does provide efficacy in naïve vaccinated pigs. Evaluation of the percentage of ilea samples with microscopic lesions indicated that 95% of the pigs in Group 5 had lesions and this group is again significantly (P<0.05) different from Groups 2 and 4. Group 5 had an average microscopic colon score of 1.35 and 60% of the animals in this treatment group were positive for *Lawsonia* lesion detection. This was significantly (P<0.05)

TABLE 2

Summary of gross lesion scores among treatment groups in pigs

| Group | Group Treatment | Ileum (Pos/Group Total) | Ileum Gross Score | Colon (Pos/Group Total) | Colon Gross Score |
|---|---|---|---|---|---|
| 1 | Sow A - Pig vaccinated | 3/19[b] | 0.16[b] | 2/19 | 0.26 |
| 2 | Sow A - Pig placebo | 9/20[b,d] | 0.85[b,d] | 4/20 | 0.45 |
| 3 | Sow A - Strict Control | 0/10[f] | 0.00[f] | 0/10[f] | 0.00[f] |
| 4 | Sow B - Pig vaccinated | 3/20[e] | 0.15[e] | 1/20[e] | 0.05[e] |
| 5 | Sow B - Pig placebo | 16/20[d,e] | 2.35[d,e] | 6/20[e] | 0.80[e] |
| 6 | Sow B - Strict control | 0/10[f] | 0.00[f] | 0/10[f] | 0.00[f] |

[b]Group 1 and 2 comparison is significantly (P < 0.05) different.
[c]Group 1 and 4 comparison is significantly (P < 0.05) different.
[d]Group 2 and 5 comparison is significantly (P < 0.05) different.
[e]Group 4 and 5 comparison is significantly (P < 0.05) different.
[f]Group not included in the statistical analysis as indicated in the protocol.

IHC and H&E methods were used to evaluate microscopic piglet lesion development. Sections 2-4 cm in length of tonsil, more than both the Group 2 and 4 treatment groups. The macroscopic data is summarized in Table 3.

TABLE 3

Summary of microscopic lesions in pig tissues at the termination of the study

| Group | Group Treatment | ILEUM Average Microscopic (IHC) Lesion Scores | ILEUM (Severity) Pigs IHC Positive for Micro-Lesions/ Group Total | COLON Average Microscopic (IHC) Lesion Scores | COLON (Severity) Pigs IHC Positive for Micro- Lesions/ Group Total |
|---|---|---|---|---|---|
| 1 | Sow A - Pig vaccinated | 0.35 | 3/20 | 0.15 | 2/20 |
| 2 | Sow A - Pig placebo | 0.70[d] | 6/20[d] | 0.55[d] | 5/20[d] |
| 3 | Sow A - Strict Control | 0.00[f] | 0/10[f] | 0.00[f] | 0/10[f] |
| 4 | Sow B - Pig vaccinated | 0.15[e] | 2/20[e] | 0.05[e] | 1/20[e] |
| 5 | Sow B - Pig placebo | 2.42[d,e] | 18/19[d,e,*] | 1.35[d,e] | 12/20[d,e] |
| 6 | Sow B - Strict Control | 0.20[f] | 1/10[f] | 0.00[f] | 0/10[f] |

[d]Group 2 and 5 comparison is significantly (P < 0.05) different.
[e]Group 4 and 5 comparison is significantly (P < 0.05) different.
[f]Group not included in the statistical analysis as indicated in the protocol.
*1 Sample had severe necrosis and sloughing and could not be read by IHC.

In order to evaluate piglet fecal shedding of *Lawsonia* by f-PCR, fecal swabs were collected weekly from all test animals in each treatment group and tested for the presence of *L. intracellularis* by Ileitis PCR on days 21, 28, 35, 42, 49, 56, and 63 of the study. On days 21, 28, and 35, piglets in all treatment groups were f-PCR negative for *L. intracellularis*. Group 1 piglets were detected as f-PCR positive on day 42 and remained positive until day 63 with 11-16% of the piglets testing positive during this time period. Group 2 piglets were detected as f-PCR positive on day 49 and remained positive until day 63 with 5-25% of the piglets testing positive during this time period. Group 4 piglets were detected as f-PCR positive on day 42 and remained positive until day 63 with 5-25% of the piglets testing positive during this time period, respectively. Group 5 piglets were detected as f-PCR positive on day 49 and remained positive until day 63 with 15-72% of the piglets testing positive during this time period. Group 3 and 6 piglets remained f-PCR negative for the duration of the trial. Chi-square analysis of the data indicates a significant ($P<0.05$) difference between groups 4 and 5 on days 42, groups 2 and 5 on day 63, and groups 4 and 5 on day 63. The fecal shedding data is summarized on Table 4.

TABLE 4

Summary of *L. intracellularis* fecal shedding among pig treatment groups

| | Groups | | | | | |
|---|---|---|---|---|---|---|
| Group Treatment | 1 Sow A - Pig vaccinated | 2 Sow A - Pig placebo | 3 Sow A - Strict control | 4 Sow B - Pig vaccinated | 5 Sow B - Pig placebo | 6 Sow B - Strict control |
| Day 21 | 0/20$^a$ | 0/20$^a$ | 0/10$^f$ | 0/20$^a$ | 0/20$^a$ | 0/10$^f$ |
| Day 28 | 0/20$^a$ | 0/20$^a$ | 0/10$^f$ | 0/20$^a$ | 0/20$^a$ | 0/10$^f$ |
| Day 35 | 0/20$^a$ | 0/20$^a$ | 0/10$^f$ | 0/20$^f$ | 0/20$^a$ | 0/10$^f$ |
| Day 42 | 3/20 | 0/20 | 0/10$^f$ | 5/20$^e$ | 0/20$^e$ | 0/10$^f$ |
| Day 49 | 2/19$^a$ | 1/20$^a$ | 0/10$^f$ | 2/20$^a$ | 3/20$^a$ | 0/10$^f$ |
| Day 56 | 2/19$^a$ | 3/20$^a$ | 0/10$^f$ | 1/20$^e$ | 8/19$^e$ | 0/10$^f$ |
| Day 63 | 3/19 | 5/20$^d$ | 0/10$^f$ | 2/20$^e$ | 13/18$^{d,e}$ | 0/10$^f$ |

$^a$Overall comparison is not significantly different by Chi-square test.
$^d$Group 2 and 5 comparison is significantly (P < 0.05) different by Chi-square test.
$^e$Group 4 and 5 comparison is significantly (P < 0.05) different by Chi-square test.
$^f$Group not included in the statistical analysis as indicated in the protocol.

*Lawsonia* tissue colonization (t-PCR) in pigs was evaluated at the termination of the study (day 63) by PCR testing of tissue sections of the terminal ileum, colon, tonsil, and mesenteric lymph node. The strict control (Groups 3 and 6) were T-PCR negative for the detection of *Lawsonia* and thereby confirm the validity of the pig source and study. All tonsil samples were T-PCR negative. Only the Group 5 colon and mesenteric lymph node samples were positive, with 5-10% of the piglets testing positive. The ilea samples from Group 1 and 2 piglets had 20% and 25% T-PCR positive test results, respectively. In comparison, piglets from Groups 4 and 5 had 5% and 45% T-PCR positive test results, respectively. All ilea samples from Groups 3 and 6 were T-PCR negative. Chi-square analysis indicated no significant differences between treatment groups in the tonsil, mesenteric lymph node, or colon samples. There was a significant difference ($P<0.05$) between Groups 4 and 5 in T-PCR results from the ileum, with Group 5 having the highest percent positive in the trial. Data from this test is summarized in Table 5.

TABLE 5

Summary of *L. intracellularis* tissue colonizing among pig treatment groups (positive/group total)

| Group | Group Treatment | Tonsil t-PCR positive | Mesenteric Lymph Node t-PCR positive | Ileum t-PCR positive | Colon t-PCR positive |
|---|---|---|---|---|---|
| 1 | Sow A - Pig vaccinated | 0/20$^a$ | 0/20$^a$ | 4/20 | 0/20$^a$ |
| 2 | Sow A - Pig placebo | 0/20$^a$ | 0/20$^a$ | 5/20 | 0/20$^a$ |
| 3 | Sow A - Strict control | 0/10$^f$ | 0/10$^f$ | 0/10$^f$ | 0/10$^f$ |
| 4 | Sow B - Pig vaccinated | 0/20$^a$ | 0/20$^a$ | 1/20$^e$ | 0/20$^a$ |
| 5 | Sow B - Pig placebo | 0/20$^a$ | 2/20$^a$ | 9/20$^e$ | 1/20$^a$ |
| 6 | Sow B - Strict control | 0/10$^f$ | 0/10$^f$ | 0/10$^f$ | 0/10$^f$ |

$^a$Overall comparison is not significantly different by Chi-square test.
$^e$Group 4 and 5 comparison is significantly (<0.05) different by Chi-square test.
$^f$Group not included in the statistical analysis as indicated in the protocol.

ADWG was calculated from the time of vaccination (day 21), to challenge administration (day 42), to the termination of the study (day 63), and between challenge (day 42) and study termination (day 63). On the day of vaccination (day 21), there was no significant difference between treatment groups. Similarly, there was no significant difference following vaccination from day 21 to day 42. Such a result confirms that the vaccine is safe and does not impact performance as measured by weight gain. Following virulent challenge, there were significant differences ($P<0.05$) in ADWG between Groups 1 and 4, Groups 2 and 5, and Groups 4 and 5. Group 5 had the lowest ADWG in the study at 0.88 lb/day. Chi-square evaluation of the time period from vaccination through challenge and up to the time of study termination also indicated a significant difference ($P<0.05$) between Groups 1 and 4 and Groups 4 and 5. This data is summarized below in Table 6.

TABLE 6

Average daily weight gains (ADWG) of pigs

| Group | Group Treatment | Average Initial Weight (lbs.) on day 21 | ADWG (day 21–42) (lbs.) Vaccination | ADWG (day 42–63) (lbs.) Challenge | Total ADWG (day 21 to day 63) (lbs.) Vaccination through Challenge |
|---|---|---|---|---|---|
| 1 | Sow A - Pig vaccinated | 14.4$^a$ | 0.90$^a$ | 0.99$^c$ | 0.94$^c$ |
| 2 | Sow A - Pig placebo | 14.0$^a$ | 0.88$^a$ | 1.01$^d$ | 0/94 |
| 3 | Sow A - Strict control | 14.8$^f$ | 1.01$^f$ | 1.14$^f$ | 1.08$^f$ |

TABLE 6-continued

Average daily weight gains (ADWG) of pigs

| Group | Group Treatment | Average Initial Weight (lbs.) on day 21 | ADWG (day 21–42) (lbs.) Vaccination | ADWG (day 42–63) (lbs.) Challenge | Total ADWG (day 21 to day 63) (lbs.) Vaccination through Challenge |
|---|---|---|---|---|---|
| 4 | Sow B - Pig vaccinated | 14.2$^a$ | 0.97$^a$ | 1.12$^{c,e}$ | 1.05$^{c,e}$ |
| 5 | Sow B - Pig placebo | 13.4$^a$ | 0.90$^a$ | .088$^{d,e}$ | 0.88$^e$ |
| 6 | Sow B - Strict control | 14.0$^f$ | 1.00$^f$ | 1.10$^f$ | 1.05$^f$ |

$^a$Overall comparison is not significantly different by Chi-square test.
$^c$Group 1 and 4 comparison is significantly (P < 0.05) different by Chi-square test.
$^d$Group 2 and 5 comparison is significantly (P < 0.05) different by Chi-square test.
$^e$Group 4 and 5 comparison is significantly (P < 0.05) different by Chi-square test.
$^f$Group not included in the statistical analysis as indicated in the protocol.

Clinical observations of the piglets were recorded on a daily basis for each animal from the day of challenge (day 42) to the termination of the study (day 63). Clinical scores were calculated to obtain an average daily clinical score which reflected the severity and duration of sickness among treatment groups due to challenge by a virulent *Lawsonia* isolate. A score of 3 was indicative of a normal, healthy animal. There were few clinical scores other than "3" in any of the groups following virulent challenge, and there was not a significant difference between any of the treatment groups. Average clinical scores for each treatment group are summarized below in Table 7.

TABLE 7

Average clinical scores of pigs

| Treatment Group | Group Identification | Average Clinical Score |
|---|---|---|
| 1 | Sow A - Pig vaccinated | 3.01$^a$ |
| 2 | Sow A - Pig placebo | 3.00$^a$ |
| 3 | Sow A - Strict control | 3.00$^f$ |
| 4 | Sow B - Pig vaccinated | 3.01$^a$ |
| 5 | Sow B - Pig placebo | 3.02$^a$ |
| 6 | Sow B - Strict control | 3.00$^f$ |

$^a$Overall comparison is not significantly different.
$^f$Group not included in the statistical analysis as indicated in the protocol.

Piglet serological evaluation via IFAT testing for the presence of anti-*Lawsonia* IgG antibodies was performed on serum samples that were collected weekly from all test animals. The serum samples were collected on days 0, 7, 14, 21, 28, 35, 42, 49, 56, and 63. Prior to challenge, some piglets in Groups 1-3 were seropositive for *Lawsonia*, thereby confirming that some maternal immunity was induced during sow vaccination. In contrast, all piglets in Groups 4-6 were seronegative for *Lawsonia*. Piglets in Group 1 had significantly higher (P<0.05) numbers of seropositive animals, as compared to Group 4, on the day of farrowing and on days 7 and 14. Piglets in Group 1 were also significantly different (P<0.05) from Group 2 on day 63 of the trial. Group 2 had significantly higher (P<0.05) numbers of seropositive animals, as compared to Group 5, on days 7, 14, and 28. Maternal antibody detection lasted until day 28 in Groups 1-3. All animals in Groups 1-3 were seronegative by day 35. Following virulent challenge, there was some seroconversion detected in Groups 1, 2, 4, and 5. There was a significant difference (P<0.05) noted between Groups 1 and 4 on day 56 of the trial. Seroconversion rates for each group are summarized below in Table 8.

TABLE 8

Summary of seroconversion rates among pig treatment groups

| | Groups | | | | | |
|---|---|---|---|---|---|---|
| Group Treatment | 1 Sow A - Pig vaccinated | 2 Sow A - Pig placebo | 3 Sow A - Strict control | 4 Sow B - Pig vaccinated | 5 Sow B - Pig placebo | 6 Sow B - Strict control |
| Farrow | 5/20$^c$ | 3/20 | 1/10$^f$ | 0/20$^c$ | 0/20 | 0/10$^f$ |
| Day 7 | 7/20$^c$ | 4/20$^d$ | 3/10$^f$ | 0/20$^c$ | 0/20$^d$ | 0/10$^f$ |
| Day 14 | 5/20$^c$ | 4/20$^d$ | 3/10$^f$ | 0/20$^c$ | 0/20$^d$ | 0/10$^f$ |
| Day 21 | 2/20$^a$ | 3/20$^a$ | 2/10$^f$ | 0/20$^a$ | 0/20$^a$ | 0/10$^f$ |
| Day 28 | 3/20 | 4/20$^d$ | 3/10$^f$ | 0/20$^a$ | 0/20$^a$ | 0/10$^f$ |
| Day 35 | 0/20$^a$ | 0/20$^a$ | 0/10 | 0/20$^a$ | 0/20$^a$ | 0/10$^f$ |
| Day 42 | 0/20$^a$ | 0/20 | 0/10 | 1/20$^a$ | 0/20 | 0/10$^f$ |
| Day 49 | 0/19 | 0/20 | 0/10$^f$ | 2/20$^a$ | 1/20$^a$ | 0/10$^f$ |
| Day 56 | 0/19$^{a,c,*}$ | 1/20$^a$ | 0/10$^f$ | 4/20$^{a,c}$ | 2/19$^{a,*}$ | 0/10$^f$ |
| Day 63 | 0/19$^{a,b,c,*}$ | 8/20$^b$ | 0/10$^f$ | 5/20 | 9/18* | 0/10$^f$ |

$^a$Overall comparison is not significantly different by Chi-square test.
$^b$Group 1 and 2 comparison is significantly (P < 0.05) different by Chi-square test.
$^c$Group 1 and 4 comparison is significantly (P < 0.05) different by Chi-square test.
$^d$Group 2 and 5 comparison is significantly (P < 0.05) different by Chi-square test.
$^f$Group not included in the statistical analysis as indicated in the protocol.
*Animal death occurred in this treatment group.

Discussion

This study evaluated the safety of a *Lawsonia* vaccine in sows following high-titered, repeated doses of the vaccine during the second and third stages of gestation, that were intended to induce a high level of maternal antibody response. There was no *Lawsonia* detected in the tissues by IHC, T-PCR, or indications of *Lawsonia* infection as measured by gross pathology in any of the vaccinated sows. Furthermore, there was no fecal shedding of *Lawsonia* detected in any of the vaccinated sows. Finally, vaccinated sows had numerically higher numbers of live-healthy piglets. Accordingly, all indications are that the vaccine is safe in pregnant animals.

This complex study involved both *Lawsonia*-positive (Group A) and *Lawsonia*-negative sows (Group B), from which farrowed piglets were subsequently vaccinated (Groups 1 and 4) or not vaccinated (Groups 2 and 5). Piglets in Groups 3 and 6 served as strict controls and received no treatment or challenge exposure. Analysis of the data and subsequent conclusions were made by comparing treatment groups that varied by only a single variable (piglet vaccination or sow vaccination).

Vaccine efficacy in naïve piglets confirms that the pig source was susceptible, and that vaccination of these piglets provided efficacy against virulent heterologous challenge. This required a comparison of Group 4 (vaccinated) and Group 5 (non-vaccinated), both of which were derived from Lawsonia-negative sows. The data indicated that Group 4 was significantly different (P<0.05) from Group 5 in average gross ileum scores, average gross colon scores, fecal shedding (f-PCR), tissue colonization of the ileum (t-PCR) and ADWG. As a side note, this study also confirmed that Enterisol Ileitis B3903 provides efficacious protection after a single administration. It further confirms and validates that the source of pigs used in the trial was susceptible to heterologous virulent challenge exposure.

The comparison of Group 2 (piglets from sow Group A) and Group 5 (piglets from sow Group B) allowed the evaluation of potential maternal protection derived from sow vaccination. The data indicated that there were significant differences (P<0.05) between Groups 2 and 5 in average gross ileum scores, average microscopic ileum and colon scores, fecal shedding (f-PCR), ADWG, and serology. This data also indicated that there was some form of maternal immunity that provides protection against virulent challenge exposure for at least six weeks after birth. The study further measured serology (IFA) and found that seropositive piglets could be detected in Groups 1-3 from the day of farrowing until day 28. On an interesting note, on the day of challenge, all pigs in all groups were seronegative using the IFA assay, possibly implying that the assay used in this trial does not provide an accurate indicator of immunity against virulent Lawsonia exposure. Given the nature of the etiological agent as a mucosal pathogen and the use of an avirulent live vaccine, it is possible that some form of cellular immunity may be a factor.

Another objective of this study was to determine whether or not efficacious vaccination in the face of maternal immunity could be accomplished by vaccination of piglets earlier than is conventionally recommended or done. For this test, efficacious vaccination of piglets 16-26 days of age was confirmed. This determination was made by comparing Group 1 (piglets vaccinated from sow Group A) and Group 2 (non-vaccinated piglets from sow Group A). The primary parameters used for the comparison were macroscopic (gross) and microscopic lesions associated with the ileum and colon. The average gross ileum scores were 0.16 and 0.85 for Groups 1 and 2, respectively, which was significantly different (P<0.05). The percentage of ilea samples with gross lesions was 16% and 45% for Groups 1 and 2, respectively, and this was also significantly different (P<0.05). Group 1 piglets also had numerically, although not statistically different, lower gross colon scores, lower microscopic lesions of the ileum and colon, and less tissue colonization (t-PCR). In total, this data confirms that vaccination does provide efficacious protection above and beyond maternal immunity alone.

All but one of the other group comparisons discussed above were based on a single study variable, either sow vaccination or piglet vaccination, but not both. The comparison between Groups 1 and 5 required the evaluation of the data in the face of two study variables (sow vaccination and piglet vaccination). It is noted that Groups 2 and 5 were statistically different (P<0.05) in some parameters and numerically lower in several others. It can be reasonably assumed that Groups 1 and 5 would be statistically different in most of the study parameters as Groups 2 and 5. In summary, Groups 1 and 5 were determined to be significantly different (P<0.05) in numerous parameters including the primary study parameters of gross ileum scores, microscopic ileum scores, and microscopic colon scores.

Finally, Groups 3 and 6 (the strict control groups) confirmed pig status relative to Lawsonia and validated the pig sources. These groups were not included in the statistical analysis. All parameters measured and evaluated confirm these animals were Lawsonia-negative, except for the microscopic lesion scores of a single pig from Group 6, which was recorded as being Lawsonia-positive. Based on the cumulative data from all other parameters, it is believed that this was an error.

We claim:

1. A method of providing increased protection against Lawsonia intracellularis infection in an animal with a single dose of vaccine comprising the steps of:
   administering a single effective dose of a modified live Lawsonia intracellularis vaccine to said animal between 10-12 days of age, wherein said single effective dose induces a protective humoral and cell mediated immune response after a single administration to said animal.

2. The method of claim 1, said single effective dose comprising between $10^3$ to $10^9$ of Lawsonia intracellularis bacterium per dose.

3. The method of claim 1, said single effective dose comprising between $3.0\,TCID_{50}$ to $6.0\,TCID_{50}$ of Lawsonia intracellularis bacterium per dose.

4. The method of claim 1, said animal being a pig.

5. The method of claim 1, said administration consisting essentially of a single dose of said vaccine.

6. The method of claim 1, said administration being by oral drench.

7. The method of claim 1, further comprising the step of vaccinating the mother of said animal with said vaccine while said mother is pregnant with said animal.

8. The method of claim 7, said vaccination of the mother of said animal occurring during the second or third stages of gestation of said animal.

9. The method of claim 7, said mother being vaccinated with repeated doses of vaccine prior to farrowing said animal.

10. The method of claim 9, said mother receiving three vaccinations with said first vaccination occurring between 50 and 60 days prior to farrowing said animal 11. The method of claim 10, said second vaccination occurring between 30 and 40 days prior to farrowing said animal.

12. The method of claim 10, said third vaccination occurring between 10 and 20 days prior to farrowing said animal.

13. The method of claim 7, said vaccine comprising a high dose of Lawsonia intracellularis antigen.

14. The method of claim 13, said high dose comprising an amount of Lawsonia intracellularis antigen that is at least three fold higher than conventional amounts of Lawsonia antigen used in vaccines.

15. The method of claim 1, said modified live Lawsonia intracellularis bacteria being selected from the group consisting of ATCC Accession No. PTA-4926, ATCC Accession No. 55783, and combinations thereof.

16. A method of providing increased protection against Lawsonia intracellularis infection in an animal with a single dose of vaccine comprising the steps of:
   administering a single effective dose of a modified live Lawsonia intracellularis vaccine to said animal between 10-14 days of age, wherein said single effective dose induces a protective humoral and cell mediated immune response after a single administration to said animal.

17. A method of providing increased protection against Lawsonia intracellularis infection in an animal with a single dose of vaccine comprising the steps of:
   administering a single effective dose of a modified live Lawsonia intracellularis vaccine to said animal between 10-14 days of age, wherein said single effective dose induces a protective humoral and cell mediated immune response after a single administration to said animal, and vaccinating the mother of said animal with said vaccine while said mother is pregnant with said animal.

18. A method of providing increased protection against *Lawsonia intracellularis* infection in an animal with a single dose of vaccine comprising the steps of:

administering a single effective dose of a modified live *Lawsonia intracellularis* vaccine to said animal between 10-14 days of age, wherein said single effective dose induces a protective humoral and cell mediated immune response after a single administration to said animal, and vaccinating the mother of said animal with said vaccine while said mother is pregnant with said animal during the second or third stages of gestation of said animal.

19. A method of providing increased protection against *Lawsonia intracellularis* infection in an animal with a single dose of vaccine comprising the steps of:

administering a single effective dose of a modified live *Lawsonia intracellularis* vaccine to said animal between 10-14 days of age, wherein said single effective dose induces a protective humoral and cell mediated immune response after a single administration to said animal, and vaccinating the mother of said animal with said vaccine while said mother is pregnant with said animal, wherein the mother is vaccinated with repeated doses of vaccine prior to farrowing said animal.

* * * * *